United States Patent
Khamar et al.

(10) Patent No.: US 9,474,727 B2
(45) Date of Patent: Oct. 25, 2016

(54) PHARMACEUTICAL COMPOSITIONS OF CURCUMIN

(75) Inventors: Bakulesh Mafatlal Khamar, Ahmedabad (IN); Ashish Premkumar Gogia, Ahmedabad (IN); Chirag Chandrakant Goda, Ahmedabad (IN); Dinesh Balkunje Shenoy, Ahmedabad (IN); Rajneesh Ramesh Shrivastava, Ahmedabad (IN); Vandana Bharat Patravale, Ahmedabad (IN); Indravadan Ambalal Modi, Ahmedabad (IN); Ritu Nitin Laddha, Ahmedabad (IN); Imran Ahmad Khan, Ahmedabad (IN); Rajiv Indravadan Modi, legal representative, Ahmedabad (IN)

(73) Assignee: Cadila Pharmaceuticals Limited, Ahmedabad (IN)

( * ) Notice: Subject to any disclaimer, the term of this patent is extended or adjusted under 35 U.S.C. 154(b) by 580 days.

(21) Appl. No.: 13/822,539

(22) PCT Filed: Sep. 12, 2011

(86) PCT No.: PCT/IB2011/053974
§ 371 (c)(1),
(2), (4) Date: May 10, 2013

(87) PCT Pub. No.: WO2012/035480
PCT Pub. Date: Mar. 22, 2012

(65) Prior Publication Data
US 2013/0225689 A1    Aug. 29, 2013

(30) Foreign Application Priority Data

Sep. 15, 2010  (IN) .......................... 2553/MUM/2010

(51) Int. Cl.
| | | |
|---|---|---|
| *A61K 31/12* | (2006.01) | |
| *A61K 9/107* | (2006.01) | |
| *A61K 47/14* | (2006.01) | |
| *A61K 47/44* | (2006.01) | |
| *A61K 31/21* | (2006.01) | |
| *A61K 31/121* | (2006.01) | |

(52) U.S. Cl.
CPC ............. *A61K 31/12* (2013.01); *A61K 9/1075* (2013.01); *A61K 31/121* (2013.01); *A61K 47/14* (2013.01); *A61K 47/44* (2013.01)

(58) Field of Classification Search
CPC ...... A61K 31/12; A61K 47/14; A61K 47/44; A61K 9/1075
See application file for complete search history.

(56) References Cited

U.S. PATENT DOCUMENTS

| | | |
|---|---|---|
| 2008/0138400 A1 | 6/2008 | Kurzrock et al. |
| 2009/0324703 A1 | 12/2009 | Frautschy et al. |
| 2010/0216859 A1 | 8/2010 | Chen |

FOREIGN PATENT DOCUMENTS

| | | | |
|---|---|---|---|
| CN | 100352430 C | | 12/2007 |
| CN | 101627969 A | * | 1/2010 |
| WO | 2007103435 A3 | | 9/2007 |
| WO | 2010010431 A1 | | 1/2010 |

OTHER PUBLICATIONS

English translation of CN 100352430 C. Original Publication Date: Dec. 5, 2007; Translation Date: Jul. 12, 2015.*
Machine Translatoin of CN 101627969 A—Original Publication Date: Jan. 2010; Translation Date: Jan. 23, 2016.*
Derwent Abstract of CN 101627969 A—Original Publication Date: Jan. 2010.*
M. J. Lawrence et al., Chemistry and Physics of Lipids, vol. 82, Issue 2, Aug. 19, 1996, pp. 89-100.
PCT/IB2011/053974 International Search Report dated May 7, 2012.
Zebib et al., "Stabilization of Curcumin by Complexation with Divalent Cations in Glycerol/Water System," Bioinorganic Chemistry and Applications, vol. 2010, Article ID 292760, 1-8.
Garcea et al., "Detection of curcumin and its metabolites in hepatic tissue and portal blood of patients following oral administration," British Journal of Cancer (2004) 29, 1011-1015.

\* cited by examiner

*Primary Examiner* — Sreeni Padmanabhan
*Assistant Examiner* — Jody Karol
(74) *Attorney, Agent, or Firm* — Pepper Hamilton LLP

(57) ABSTRACT

The present invention relates to stable liquid pharmaceutical compositions of curcumin or its pharmaceutically acceptable salts or its derivatives with higher curcumin concentration and improved bioavailability without the use of buffer and/or molecular aggregation inhibitor(s). In accordance with present invention the curcumin is in the solubilized form to make a stable liquid pharmaceutical composition.

12 Claims, 1 Drawing Sheet

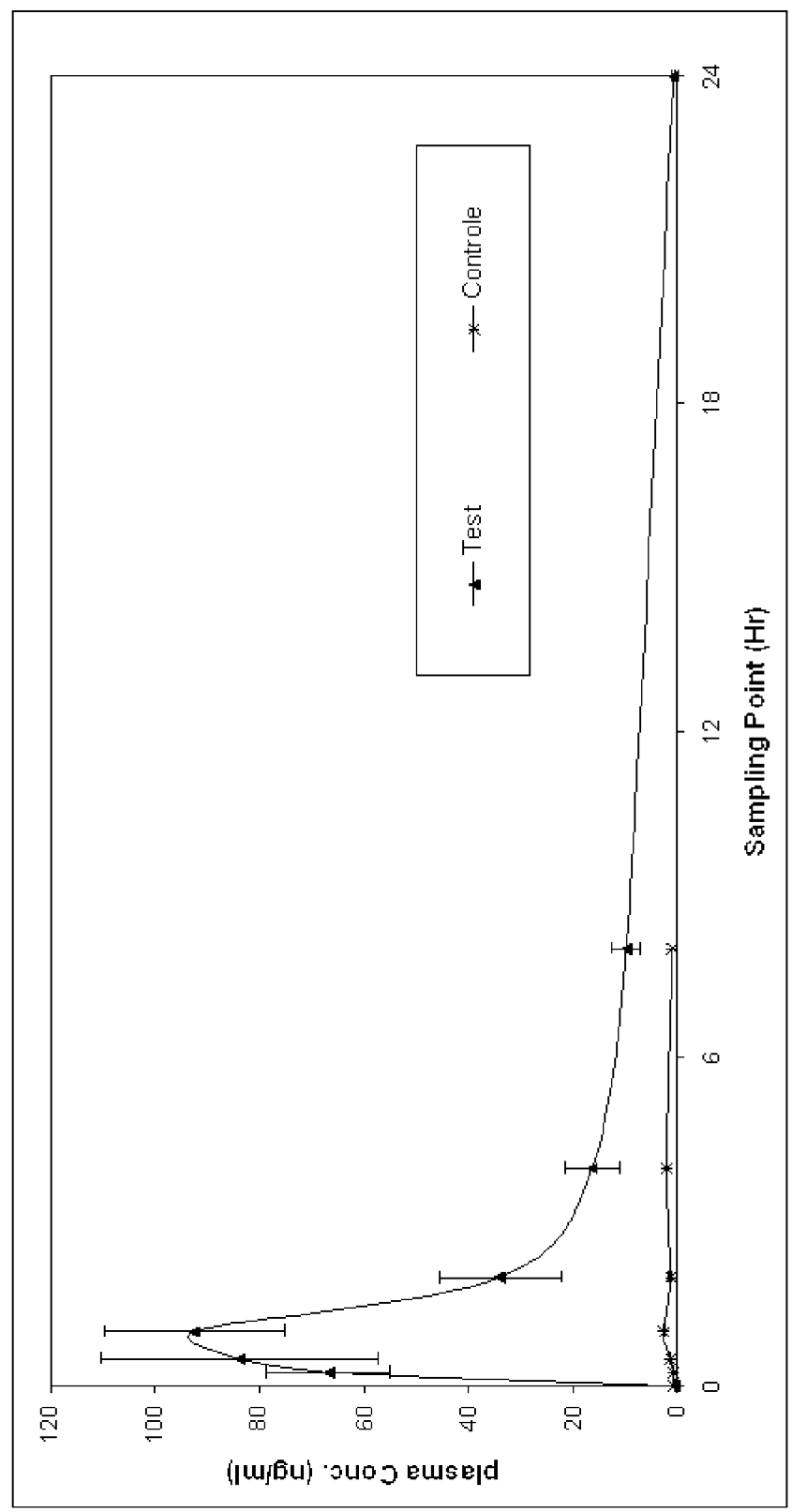

PHARMACEUTICAL COMPOSITIONS OF CURCUMIN

This application is a national phase filing under 35 U.S.C. §371 of International Patent Application No. PCT/IB2011/053974, filed Sep. 12, 2011, which claims the benefit of Indian Patent Application No. 2553/MUM/2010, filed Sep. 15, 2010, each of which is incorporated herein by reference in its entirety.

FIELD OF THE INVENTION

The present invention is related to stable liquid pharmaceutical compositions of curcumin or its pharmaceutically acceptable salts or its derivatives.

BACKGROUND OF THE INVENTION

Curcumin, a potent natural anti-oxidant and anti-inflammatory agent, has shown therapeutic potential against many diseases. These include cancers (colon, prostate, breast, skin, leukemia, etc.), atherosclerosis, stroke, CNS alcohol toxicity, traumatic brain injury, Huntington's disease, Marie-Charcot Tooth, multiple sclerosis and Alzheimer's disease.

Curcumin in this specification is referred as total curcuminoids containing curcumin, desmethoxycurcumin and bis-desmethoxycurcumin.

Curcumin is a crystalline compound and poorly soluble in water at pH less than 7. Major reasons contributing to the lower plasma and tissue levels of curcumin are due to poor absorption, high first pass metabolism and rapid systemic elimination. Most of the curcumin is not absorbed and simply passes through the GI tract and is excreted. Garcea, G. et al. (2004) reported that patients taking 3.6 g of curcumin a day (as a standard powder supplied by Sabinsa Corporation), drug levels in blood and liver were found to be negligible.

Curcumin is not soluble at acidic pH and breaks down in solution at neutral or alkaline pH (e.g., in the GI tract, after the small intestine), In addition, curcumin is susceptible to rapid glucuronidation/sulfation.

WO2007103435 discloses the compositions comprising curcuminoid, antioxidant (to stabilize curcumin against hydrolysis), water-soluble pharmaceutically acceptable carrier and optionally glucuronidation inhibitor. The said formulation with 35% w/w curcumin resulted in improved bioavailability.

CN100352430C discloses self-micro-emulsified curcumin preparation comprising curcumin, surfactant, co-surfactant, oil phase and solid adsorbent providing self-micro-emulsified system having liquid drops with size below 100 nm. Such compositions show increase in curcumin solubility and absorption in gastrointestinal tract with higher bioavailability. The concentration of curcumin in composition is in the range of 0.33 to 1.56% w/v.

WO2010010431 discloses self nano-emulsion compositions comprising curcumin (0.1 to 10% w/w), a lipidic carrier system with a hydrophilic-lipophilic balance (HLB) between 3 to 14 and a pH buffer. The lipidic carrier system is selected from one or more mono- and di-esters of saturated or unsaturated long chain fatty acids with low and medium molecular weight polyoxyethylene glycerol ethers or combinations thereof. The composition further comprises molecular aggregation inhibitor(s), a surface active agent and a co-solvent. The group of excipients used as lipidic carrier system belongs to alkyl-glycerol ether surfactants category (M. J. Lawrence et. al. Chemistry and Physics of Lipids, Volume 82, Issue 2, 19 Aug. 1996, Pages 89-100) that led to increase in overall surfactant concentration up to 90% of the formulation. The higher concentration of surfactants in the formulation is undesirable as they are likely to cause gastric irritation and gastric mucosal damage.

There is an unmet need to develop stable liquid pharmaceutical composition of curcumin or its pharmaceutically acceptable salts or its derivatives with higher curcumin concentration, without using acid buffer and/or molecular aggregation inhibitor(s) and without using high concentration of surfactants.

SUMMARY OF INVENTION

The main object of the invention is to provide stable liquid pharmaceutical compositions of curcumin or its pharmaceutically acceptable salts or its derivatives with higher curcumin concentration and improved bioavailability.

Another object of the invention is to provide stable pharmaceutical compositions wherein the concentration of curcumin in solution is 2 to 20% w/w.

Another object of the invention is to provide the said pharmaceutical compositions without the use of pH buffer and/or molecular aggregation inhibitor(s).

Further object of the invention is to provide a process for the preparation of the said pharmaceutical compositions.

DETAILED DESCRIPTION OF THE DRAWING

FIG. 1 represents comparative bioavailability study of different pharmaceutical compositions of curcumin in rats (n=6).

DETAILED DESCRIPTION OF THE INVENTION

In accordance with this invention the stable liquid pharmaceutical compositions with higher curcumin concentration comprises of curcumin or pharmaceutically acceptable salts or derivatives thereof, surfactant, solvent, oil and optionally antioxidant wherein the concentration of surfactant is not more than 60% w/w.

The compositions comprise 2 to 20% w/w of curcumin, oil, solvent, surfactant and optionally antioxidant, wherein the ratio of oil to solvent, surfactant to solvent and surfactant to curcumin is in the range of 0.83 to 10, 1 to 60 and 3 to 15, respectively.

The said composition is prepared without the use of pH buffer and/or molecular aggregation inhibitor(s).

The oil is selected from: (1) fractionated coconut oil, caprylic/capric triglyceride or oil containing fatty acid triglycerides, preferably medium chain fatty acid triglycerides (2) isopropyl myristate, isopropyl palmitate, ethyl linoleate or oil containing ethyl oleate esters of fatty acids and monovalent alkanols (3) propyleneglycol dicaprylate, propyleneglycol dilaurate or oil containing propyleneglycol di-fatty acid esters.

The surfactant is selected from polysorbate, vitamin E TPGS and cremophor, preferably cremophor.

The solvent is selected from glycofurol, polyethylene glycol (PEG 200, 400), glycerol, polypropylene glycol, propylene glycol, N-methyl-2-pyrolidone and ethyl alcohol or mixture thereof, preferably from propylene glycol and ethyl alcohol or mixture thereof.

The anti-oxidant is selected from ascorbyl palmitate, butylhydroxyanisole, butylhydroxytoluene, propyl gallate, sodium ascorbate, tocopheryl derivative such as alpha-tocopherol and mixtures thereof.

The pharmaceutical composition as per the invention shows improved bioavailability.

The present invention provides a process for the preparation of the said composition comprising
  (i) dispersing curcumin in solvent;
  (ii) adding surfactant to the curcumin dispersion of step (i);
  (iii) dissolving curcumin by mixing and heating; and
  (iv) adding oil to the solution of step (iii) to obtain the liquid pharmaceutical composition.

In one embodiment a process for the preparation of the said composition comprising:
  (i) dispersing curcumin in surfactant;
  (ii) adding solvent to the curcumin dispersion of step (i); and dissolving curcumin by mixing and heating; and
  (iii) mixing oil to the solution of step (ii) to obtain the stable liquid pharmaceutical composition.

In another embodiment a process for the preparation of the said composition comprising:
  (i) dispersing curcumin in oil;
  (ii) adding solvent to the curcumin dispersion of step (i); and
  (iii) mixing surfactant to the dispersion of step (ii) and dissolving curcumin by mixing and heating to obtain the stable liquid pharmaceutical composition.

In another embodiment a process for the preparation of the said composition comprising:
  (i) mixing solvent, surfactant and oil;
  (ii) adding curcumin to blend of step (i) and dissolving curcumin by mixing and heating to obtain stable liquid pharmaceutical composition.

The compositions according to the present invention can be administered by oral, topical or parenteral route; preferably the compositions are administered by oral route.

The invention is further illustrated with following non-limiting examples.

Example 1

A pharmaceutical composition of curcumin was prepared as given in table 1.

TABLE 1

Composition for example 1

| S. No. | Ingredients | Qty (% w/w) |
| --- | --- | --- |
| 1. | Curcumin | 5.00 |
| 2. | Cremophor RH 40 (Polyoxyl Hydrogenated Castor Oil) | 47.00 |
| 3. | Crodamol GTCC (Caprylic/Capric Triglycerides) | 25.00 |
| 4. | Ethyl Alcohol | 9.20 |
| 5. | Alpha-Tocopherol | 0.47 |
| 6. | Propylene Glycol | 13.33 |

1. Curcumin was dispersed in ethyl alcohol and propylene glycol.
2. Cremophore RH 40 was added to curcumin dispersion of step 1 with mixing and heating to dissolve the curcumin.
3. Crodamol GTCC, and alpha-tocopherol were added to the mixture of step 2 and mixed.

The formulation after dilution with water (1:1000) or 0.1 N HCl (1:1000) resulted in clear and stable solution. Particle size of resulting micro-emulsion was found below 100 nm after dilution of 24 Hr.

Example 2

A pharmaceutical composition of curcumin was prepared as given in table 2.

TABLE 2

Composition for example 2

| S. No. | Ingredients | Qty (% w/w) |
| --- | --- | --- |
| 1. | Curcumin | 21.00 |
| 2. | Cremophor RH 40 (Polyoxyl hydrogenated castor oil) | 35.00 |
| 3. | Crodamol GTCC (Caprylic/Capric Triglycerides) | 17.50 |
| 4. | Ethyl Alcohol | 15.50 |
| 5. | Propylene Glycol | 11 |

1. Curcumin was dispersed in ethyl alcohol.
2. Cremophore RH 40 was added to the curcumin dispersion of step 1 with mixing and heating to dissolve the curcumin.
3. Crodamol GTCC and propylene glycol were added to the mixture of step 2 and mixed.

Particle size of the resulting microemulsion was found to be 222 nm.

Examples 3-8

Pharmaceutical compositions of curcumin were prepared as given in table 3.

TABLE 3

Composition for examples 3-8

| S. No. | Ingredients | Example No. 3 | 4 | 5 | 6 | 7 | 8 |
| --- | --- | --- | --- | --- | --- | --- | --- |
|   |   | Qty (% w/w) | | | | | |
| 1 | Curcumin | 3 | 5 | 3 | 2 | 6 | 7.5 |
| 2 | Cremophor RH 40 | 30 | 29.40 | 59.0 | 39.2 | 46.5 | 45.8 |
| 3 | Cradamol GTCC | 4.71 | 4.60 | 37.6 | 50 | 24.7 | 24.3 |
| 4 | Ethanol | 20 | 19.60 | 0.5 | 7 | 9.1 | 9.0 |
| 5 | Vit E. Acetate | — | — | — | — | 0.5 | 0.5 |
| 6 | Propylene Glycol | 42.29 | 41.40 | — | 1.8 | 13.2 | 13.0 |
| 7 | Observation | Clear solution | Clear solution | Clear solution | Clear solution | Clear solution | Clear solution |
| 8 | Particle size (nm) | 108.5 | 1053 | 85.12 | 169.5 | 43.32 | 737.8 |

1. Curcumin was dispersed in ethyl alcohol.
2. Cremophore RH 40 was added to the curcumin dispersion of step 1 with mixing and heating.
3. Crodamol GTCC, propylene glycol were added to the mixture of step 2 and mixed.

Example 9

Pharmaceutical composition from examples 1 was further subjected to bioavailability study in rat (n=6) at dose of 150 mg/kg body weight as given in table 4.

TABLE 4

Different formulation subjected to animal study

| Groups | Pharmaceutical Composition |
| --- | --- |
| Control | drug dispersed in 2% sodium CMC |
| Test | As per example 1 |

Test demonstrated enhanced bioavailability as compared to control (FIG. 1).

Example 10

Pharmaceutical composition of example 1 was subjected to accelerated stability study as per ICH guideline. The product was found to be stable for 6 months at 40° C./75% RH as shown in table 5.

TABLE 5

Stability data at 40° C./75% RH

| Parameters | Initial | 1 M | 2 M | 3 M | 6 M |
|---|---|---|---|---|---|
| Assay | 97.1% | 92.0% | 89.2% | 90.1% | 94.8% |
| pH (10% aqueous solution) | 6.72 | 6.4 | 6.15 | 6.4 | 6.15 |
| Globule size (10% aqueous solution) | 69.92 nm | 41.90 nm | 44.00 nm | 25.05 nm | 50.88 nm |

Example 11

Pharmaceutical composition of example 1 and marketed formulations (Curcugel and Curcugel Ultra) were subjected to in vivo pharmacokinetic study in human volunteers (n=3 for each group).

The values of peak plasma concentration level ($C_{max}$) and area under the curve (AUC) obtained after administration of the pharmaceutical composition are shown in table 6.

TABLE 6

Pharmacokinetic parameters calculated from the plasma profile obtained after administration of 400 mg of pharmaceutical composition of example 1 and Curcugel 250 mg and Curcugel Ultra 500 mg in human volunteers (n = 3) each.

| Pharmacokinetic parameters | Composition as per present invention | Curcugel | Curcugel Ultra |
|---|---|---|---|
| $C_{max}$ (ng/ml) | 33.05 | Non detectable | Non detectable |
| $T_{max}$ (h) | 0.58 | — | — |
| $AUC_{0-24\ h}$ (ng/ml)h | 24.395 | — | — |
| $AUC_{0-\infty\ h}$ (ng/ml)h | 25.615 | — | — |

The pharmaceutical composition comprising curcumin, surfactant, solvent, oil and anti-oxidant was found to exhibit high bioavailability as shown in table 6.

We claim:

1. A stable pharmaceutical composition comprising:
   curcumin, oil, solvent, and surfactant, wherein the ratio of oil to solvent is about 0.83 to about 10, surfactant to solvent is about 1 to about 60, and surfactant to curcumin is about 3 to 15, with curcumin in the range of about 2 to about 20% w/w with respect to the pharmaceutical composition;
   wherein surfactant is selected from polysorbate, vitamin E TPGS and cremophor;
   wherein the composition is free of a pH buffer and a molecular aggregation inhibitor and wherein the composition comprises a single surfactant.

2. The pharmaceutical composition as claimed in claim 1 wherein oil is selected from: fractionated coconut oil, caprylic/capric triglyceride or an oil containing fatty acid triglycerides, isopropyl myristate, isopropyl palmitate, ethyl linoleate or an oil containing ethyl oleate esters of fatty acids and monovalent alkanols, propylene glycol dicaprylate, propylene glycol dilaurate or an oil containing propylene glycol di-fatty acid esters, and combinations thereof.

3. The pharmaceutical composition as claimed in claim 1 wherein the surfactant is cremophor.

4. The pharmaceutical composition as claimed in claim 1 wherein solvent is selected from glycofurol, polyethylene glycol, glycerol, polypropylene glycol, propylene glycol, glycerin, N-methyl-2-pyrolidone and ethyl alcohol or mixture thereof.

5. The pharmaceutical composition as claimed in claim 1 wherein the solvent is mixture of propylene glycol and ethyl alcohol.

6. The pharmaceutical composition as claimed in claim 1 further comprising anti-oxidant selected from ascorbyl palmitate, butylhydroxyanisole, butylhydroxytoluene, propyl gallate, sodium ascorbate, tocopherol, and mixtures thereof.

7. A pharmaceutical composition as claimed in claim 1 has improved bioavailability.

8. A process for the preparation of the pharmaceutical composition as claimed in claim 1 comprising:
   I. dispersing curcumin in solvent or the surfactant or oil;
   II. adding the surfactant or solvent to the curcumin dispersion of step (I);
   III. dissolving curcumin by mixing and heating; and
   IV. adding oil or the surfactant to the solution of step (III) to obtain the pharmaceutical composition;
   wherein the composition is prepared without the use of a pH buffer and a molecular aggregation inhibitor.

9. A process for the preparation of the pharmaceutical composition as claimed in claim 1 comprising:
   I. mixing solvent, the surfactant and oil;
   II. adding curcumin to the blend of step (I) and dissolving curcumin by mixing and heating to obtain the liquid pharmaceutical composition;
   wherein the composition is prepared without the use of a pH buffer and a molecular aggregation inhibitor.

10. The pharmaceutical composition as claimed in claim 1 is for oral or topical or parenteral route.

11. The pharmaceutical composition as claimed in claim 1 wherein the curcumin concentration is about 2 to about 10% by weight of the composition.

12. The pharmaceutical composition as claimed in claim 1, wherein the oil is an oil containing medium chain fatty acid triglycerides.

* * * * *